United States Patent
Chaudhury et al.

(10) Patent No.: US 12,383,212 B2
(45) Date of Patent: Aug. 12, 2025

(54) OPTICAL ARRANGEMENT FOR AN X-RAY SYSTEM FOR DETERMINING A PATIENT POSITION AND/OR PATIENT ROTATION

(71) Applicant: KONINKLIJKE PHILIPS N.V., Eindhoven (NL)

(72) Inventors: Sudipta Chaudhury, Bangalore (IN); Soubhik Paul, Bangalore (IN); Steffen Weiss, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 257 days.

(21) Appl. No.: 18/023,061

(22) PCT Filed: Aug. 20, 2021

(86) PCT No.: PCT/EP2021/073154
§ 371 (c)(1),
(2) Date: Feb. 24, 2023

(87) PCT Pub. No.: WO2022/043215
PCT Pub. Date: Mar. 3, 2022

(65) Prior Publication Data
US 2023/0363727 A1 Nov. 16, 2023

(30) Foreign Application Priority Data
Aug. 28, 2020 (EP) .................................. 20193365

(51) Int. Cl.
*A61B 6/08* (2006.01)
*A61B 6/00* (2006.01)
*A61B 6/04* (2006.01)

(52) U.S. Cl.
CPC .............. *A61B 6/0492* (2013.01); *A61B 6/08* (2013.01); *A61B 6/547* (2013.01)

(58) Field of Classification Search
CPC ..... A61B 1/00165; A61B 1/06; A61B 1/0605; A61B 2034/2046; A61B 2034/2055;
(Continued)

(56) References Cited

U.S. PATENT DOCUMENTS

| 9,557,158 B2 | 1/2017 | Hofmann | |
|---|---|---|---|
| 2004/0105526 A1* | 6/2004 | Zhang | A61B 6/587 378/205 |

(Continued)

FOREIGN PATENT DOCUMENTS

EP 3653124 A1 5/2020

OTHER PUBLICATIONS

PCT International Search Report, International application No. PCT/EP2021/073154, Nov. 29, 2021.

*Primary Examiner* — Don K Wong
(74) *Attorney, Agent, or Firm* — Larry Liberchuk

(57) ABSTRACT

The invention concerns an optical arrangement for an X-ray system for determining a patient position and/or a patient rotation of a patient to be X-rayed by the X-ray system, an X-ray system comprising such optical arrangement, a system for controlling and a method for determining a patient position and/or a patient rotation. The optical arrangement comprises a laser source, and a detector vertically spaced apart from each other. The laser source is configured for emitting a horizontal laser line onto the patient, the detector is configured for detecting a course of the laser line emitted onto the patient. An analysing unit configured for determining the patient position and/or the patient rotation of the patient, based on an analysis of the detected course of the laser line. The analysing unit is configured for validating whether the determined patient position and/or patient rotation of the patient corresponds to a predetermined reference parameter, and wherein the analysing unit is configured for (Continued)

generating a feedback signal based on a result of the validation.

14 Claims, 4 Drawing Sheets

(58) Field of Classification Search
CPC .... A61B 2034/2057; A61B 2034/2065; A61B 2034/2072; A61B 2034/107; A61B 5/0062; A61B 5/0066; A61B 2034/2068; A61B 90/30; G02B 21/06
See application file for complete search history.

(56) References Cited

U.S. PATENT DOCUMENTS

| | | |
|---|---|---|
| 2007/0030957 A1 | 2/2007 | Pommi |
| 2014/0348296 A1 | 11/2014 | Goossen |
| 2015/0190657 A1 | 7/2015 | Maurer, Jr. |
| 2017/0136261 A1 | 5/2017 | Hofmann |

\* cited by examiner

OPTICAL ARRANGEMENT FOR AN X-RAY SYSTEM FOR DETERMINING A PATIENT POSITION AND/OR PATIENT ROTATION

FIELD OF THE INVENTION

The invention relates to the field of optical arrangement for an X-ray system for determining a patient position and/or a patient rotation, and more specifically to an optical arrangement for a chest X-ray system, an X-ray system for generating an X-ray image and a method for determining a patient position and/or patient rotation.

BACKGROUND OF THE INVENTION

X-ray is a widely used diagnostic imaging modality to diagnose diseases in thorax regions, especially in lungs. Assessment of X-ray quality, in particular of chest radiograph quality, is an important step in radiological interpretation. In current workflows, a quality issue can only be detected during radiological image interpretation, which means after the generating of the X-ray image. This causes patient recall and retake of the X-ray image. A manual observation by the medical staff during the X-ray imaging process may not be sufficient enough to prevent quality loss of the X-ray image. Moreover, a patient recall causes additional burden to the work list of the medical staff, the technician and also to the patient itself, which has to go through an additional exposure. Reasons for patient recall and retake of the X-ray image are a wrong patient orientation and patient movements, for instance due to inhalation during the imaging process, which leads to errors in the field of view, which is the field comprising the dimensions of the exact anatomic region included in an image. The field of view gets compromised due to improper patient positioning and patent movement. Along with this, if a patient is not properly oriented for the X-ray imaging then the X-ray image does not meet the quality standards, as there may be shadows mediastinum and other section on the region of interest (ROI). A further aspect is the patient movement caused by the patient inhalation. During the X-ray imaging procedure, holding the breath properly may help imaging patient's heart and lung more clearly. Contrary, it may happens many times, that the patient inhalation is not correct or the health conditions of the patient does not support to hold breath properly for longer time. In such cases, it is not possible for the medical staff, to get information about this prior to the triggering of the X-ray image. Once, the X-ray image may be generated, then only the medical staff, or the technician, or radiologist finds out that the inhalation was wrong and has to ask for a retake.

SUMMARY OF THE INVENTION

Therefore, there exist a need for optimizing the quality of an X-ray image. In particular, there exist a need to improve the identification of patient orientation, in particular patient position and patient rotation, and patient movement due to inhalation for improving the quality of an X-ray image, such that a recall of a patient and a retake of an X-ray image can be avoided.

An object of the invention is to provide an apparatus and a methodology for real time assessment of patient position, patient rotation and patient inhalation and autonomous triggering of X-ray when the position, rotation, and/or inhalation is correct.

The object of the present invention is solved with the subject matter of the independent claims, wherein further embodiments are incorporated in the dependent claims.

According to a first aspect of the invention, an optical arrangement, which is to be used with an X-ray system for determining a patient position and/or a patient rotation of a patient to be x-rayed by the X-ray system, comprises a laser source and a detector. As will become apparent from the present disclosure, the detector is vertically spaced apart from the laser source, when the presented optical arrangement is applied for its intended purpose and when being applied for determining the patient position and/or the patient rotation of a patient together with X-ray system. The laser source is configured for emitting a horizontal laser line onto the patient, wherein the detector is configured for detecting a course of the laser line emitted onto the patient. An analyzing unit is configured for determining the patient position and/or the patient rotation of the patient, based on an analysis of the detected course of the laser line. The analyzing unit is further configured for validating whether the determined patient position and/or patient rotation of the patient corresponds to a predetermined reference parameter and wherein the analyzing unit is configured for generating a feedback signal based on a result of the validation.

In the context of the present invention, the term "patient position" shall be understood to describe a position of a patient, which shall be X-rayed by X-ray system, wherein the position refers to a location of the patient in front of the X-ray sensor. As is appreciated by the skilled reader said position may be described/defined by e.g. 3D coordinates. During the X-ray imaging a predetermined part, i.e. body portion, of the patient shall be examined, for instance the chest or the back of the patient. Hence, the patient position is relevant for the quality of the generated X-ray image. For instance, the patient may be located to be too near to one or another side of the X-ray sensor, which would cause a loss in/of information in the generated X-ray image. Therefore, a correct patient position may be e.g. a symmetrically alignment of a centerline of the patient with a centerline of the X-ray sensor. This will be explained in more detail hereinafter in the context of particular embodiments.

In the context of the present invention, the term "patient rotation" shall be understood to describe the rotation of the patient in front of the X-ray sensor, which accordingly to the patient position, may lower the quality of the generated X-ray image. Said patient rotation may describe/defined the rotational status of the patient within 3D space. For instance, the patient may be rotated to a left side or a right side in front of the X-ray sensor, which could cause a loss in image information, as the patient does not stand correct in front of the X-ray sensor. An ideal position of the patient may be a position of the patient, wherein a centerline extending through the center of the patient from the head to the feet, is in line with a centerline of the X-ray sensor, which extends vertical from a top to a bottom of the X-ray sensor.

In the context of the present invention, the term "horizontal laser lane" shall be understood to describe the location and the course of the laser line within a real setting of the optical arrangement. As is understood by the skilled reader, the horizontal line extends, when being emitted, within 3D space parallel to the horizon and/or parallel to the ground plane, at which the optical arrangement, preferably with the X-ray system, is used and applied. This will be explained in more detail hereinafter in the context of particular embodiments, especially the embodiments shown in the Figures. The laser line is emitted onto the patient, wherein the laser line extends horizontal over the patient from a left side of the patient to a right side of the patient, or vice versa. In particular, the horizontal laser line extends perpendicular to the centerline of the patient. In general, the position of the laser line is located at the chest or the back of the patient, wherein the exact position is determined by the medical staff, technician, and/or radiologist before the triggering of the X-ray image. The exact position may depend on the respective body part to be examined, whether it is a lung, a heart, etc. of the patient. In particular, the horizontal laser line is emitted onto a body surface of the patient, wherein the detector detects the course of the laser line on the body surface of the patient.

In the context of the present invention, the term "course of the laser line" shall be understood to describe the extension, spatial development, and/or spatial route of the laser line along its horizontal extension. The course of the laser line can be understood as the curvature of the laser line, wherein this curvature may be straight along the horizontal extension. On the other side, the curvature may be round or bend in a different shape, wherein this shape depends on the object or source (e.g. the patient body surface) onto which the horizontal laser line is emitted. Further, the course of the laser line may comprise gaps, or the laser line may be interrupted. In particular, the course of the laser line may be a course with and/or without the patient in front of the X-ray sensor. For instance, without a patient, the laser line is emitted onto the X-ray sensor and not onto the patient, wherein with a patient the laser line is emitted onto the patient in front of X-ray senor. In particular, the course of the laser line without the patient may be a straight horizontal line, wherein the course of the laser line emitted onto the patient is a bend horizontal line due to the presence of/based on the shape of the body surface of the patient.

In the context of the present invention, the term "vertically spaced apart" shall be understood to describe the arrangement of the laser source and the detector to each other. The laser source and the detector may be arranged above each other, wherein the laser source may be arranged above the detector or vice versa. When the laser line extends horizontally, the spaced apart arrangement of the laser source and the detector is vertically, i.e. perpendicular to the horizontal extending laser line. The vertical arrangement of the laser source and the detector may be parallel to the centerline of the patient. This will be explained in more detail hereinafter in the context of particular embodiments, especially the embodiments shown in the Figures.

In other words, with the optical arrangement presented herein, a laser based optical telemetry solution is provided for detecting and determining patient position and/or patient rotation and/or for providing a feedback. The provided feedback may be used to correct and asses patient position and patient rotation, which will be described in detail and in connection with some embodiments herein below. The patient position and the patient rotation may be determined using the same laser based approach. The detector detects the reflected radiation, i.e. the laser line, on the patient. The detector of the optical arrangement may be vertically spaced apart from the laser source in such a manner that the detector may be arranged above the laser source in the X-ray room where the patient is imaged, or vice versa. In particular, the positions of the laser source and the detector are interchangeable. A change in the emitted laser line due to a presence of the patient may get visible when the detector and the laser source are spaced apart from each other. Contrary, if the detector and the laser source would not be spaced apart, i.e. distanced from each other, for example, if they would be arranged on the same height, no change in the course of the laser line could be detected by the detector. The distance between the patient and the laser source may depend on the respective setup of the X-ray system and can be chosen by the user accordingly and using the present disclosure.

This setup may be fixed and depend on the fixed position of the X-ray sensor and the X-ray source. A preferable distance between the X-ray source and the X-ray sensor may be in the range of 1,5 m to 2 m. The laser line may be placed on a chest of the patient for anterior-posterior (AP) X-ray imaging and/or the laser line may be placed on a back of the patient for posterior-anterior (PA) X-ray imaging. According to this embodiment, the patient position and the patient rotation can be determined prior to the triggering of the X-ray image, such that it may be determined whether the patient is properly oriented in front of the X-ray sensor. Accordingly, the quality of a generated X-ray image can be assessed and positively influenced prior to the generation of the X-ray image, which reduces a recall of the patient, a retake of an X-ray imaging, and a patient exposure to X-ray radiation.

The feedback signal may be provided to the user by means of embodiments of the present optical arrangement, such that the position and/or rotation of the patient can be assessed and the user may determine based on the feedback signal whether a position and/or rotation of the patient should be corrected.

Further, the optical arrangement may comprise an interface, which is configured for providing the feedback signal to the user, wherein the interface is configured to communicate with the user and/or with the patient.

According to an exemplary embodiment of the invention, a respective and corresponding method for determining a patient position and/or a patient rotation of a patient to be X-rayed by the X-ray system is presented. The method may comprise the steps of emitting a horizontal laser line onto the patient by a laser source, detecting the course of the laser line emitted onto the patient by a detector. The method may further comprise the steps of determining the patient position and/or the patient rotation of the patient based on an analysis of the detected course of the laser line using an analyzing unit, validating whether the determined patient position and/or patient rotation of the patient corresponds to a predetermined reference parameter using the analyzing unit, and generating a feedback signal based on a result of the validation by the analyzing unit.

The predetermined reference parameter may be a parameter used for a reference position and/or rotation, which enables an improved or optimum X-ray image quality. For instance, for generating a high-quality chest X-ray image for displaying the lung the reference parameter may be a symmetrically position of the patient in front of the X-ray sensor. In particular, a centerline of the patient may be symmetrically aligned with the centerline of the X-ray sensor, wherein the centerline of the patient extends from the top (head) of the patient to the bottom (feet) of the patient.

According to an exemplary embodiment of the invention, the laser source is arranged to emit the laser line along an emitting direction, which emitting direction extends along an imaginary line from the laser source to the patient. The detector is arranged to detect the course of the laser line along a detection direction, which detection direction extends along an imaginary line from the detector to the patient, wherein the emitting direction of the laser source and the detection direction of the detector form an angle in a range between 40 to 45 degrees.

For instance, the emitting direction extends horizontal with respect to an extension direction of the X-ray sensor, in other words the imaginary line from the laser source to the patient is perpendicular to the centerline of the X-ray sensor. Consequently, the detection direction does not extend horizontal with respect to extension direction of the X-ray sensor (is not perpendicular to the centerline of the X-ray sensor). The arrangement of the respective emitting direction and detection direction may be as described above or may be arranged vice versa. Using an angle between 40 to 45 degrees allows reducing the risk that the laser line is emitted onto the eyes of the patient. Moreover, this angle may be suitable for an accurate detection of a change in the course of the laser line by the detector.

According to an exemplary embodiment of the invention, the method for determining a patient position and/or a patient rotation of a patient to be X-rayed by the X-ray system may further comprise emitting the laser line along an emitting direction by the laser source, which emitting direction extends along an imaginary line from the laser source to the patient. Detecting the course of the laser line along a detection direction by the detector, which detection direction extends along an imaginary line from the detector to the patient and wherein the emitting direction of the laser source and the detection direction of the detector form an angle in a range between 40 to 45 degrees.

According to an exemplary embodiment of the invention, the generated feedback signal is embodied as a control signal configured for controlling the patient position and/or patient rotation when being received by an X-ray system or a patient positioning system.

In particular, the control signal is received by a patient positioning system for changing the patient position and/or patient rotation upon receipt of the control signal. The feedback signal may be provided as an optic, acoustic, and/or haptic feedback signal for indicating the result of the validation, wherein respective optic, acoustic, haptic signal indicates a correct or wrong patient position and/or patient rotation. The patient positioning system may be part of the optical arrangement, or the patient positioning system may be part of the X-ray system, or the patient positioning system may be an extra part, single system provided additionally for the optical arrangement and/or the X-ray system. Whether the patient positioning system is a part of the optical arrangement or not may dependent on the respective embodiment of the invention. Nevertheless, the optical arrangement comprises the feedback signal which may be received by the additional (or single part) patient positioning system. The control signal may be configured for controlling the patient position and/or the patient rotation in such a manner that the control signal may comprise the determined patient position/patient rotation (or both) and the control signal may comprise a value from which the determined position/patient rotation differ from the reference parameter. Accordingly, the control signal may be used to correct the position/patient rotation about the difference value. In particular, the patient positioning system may use the control signal for adapting the patient position/patient rotation based on the difference value.

According to an exemplary embodiment of the invention, the method for determining a patient position and/or a patient rotation of a patient to be X-rayed by the X-ray system may further comprise controlling the patient position and/or patient rotation using the generated feedback signal which is embodied as a control signal, when being received by an X-ray system or a patient positioning system.

According to the first aspect of the invention, in the optical arrangement spatial coordinates of a vertical centerline of an X-ray sensor of the X-ray system are stored, and wherein the analyzing unit is configured for comparing the determined patient position and/or patient rotation with the stored spatial coordinates. The vertical centerline of the X-ray sensor may be embodiment as the reference parameter.

For instance, the spatial coordinates may be stored in the analyzing unit. Alternatively, the spatial coordinates may be received by the optical arrangement from an external data storage, in which the spatial coordinates may be stored. In the context of the present invention, the term "vertical centerline" shall be understood to describe a centerline of an X-ray sensor, which extends vertical in the center of the X-ray sensor. In particular, the X-ray sensor may comprise a left and a right end, wherein the centerline is equally spaced apart from both the left and the right end.

According to an exemplary embodiment of the invention, the method for determining a patient position and/or a patient rotation of a patient to be X-rayed by the X-ray system may further comprise storing in the optical arrangement spatial coordinates of a vertical centerline of an X-ray sensor of the X-ray system. Comparing the determined patient position and/or patient rotation with the stored spatial coordinates using the analyzing unit, wherein the vertical centerline of the X-ray sensor is the reference parameter.

According to an exemplary embodiment of the invention, in the optical arrangement spatial coordinates of a left upper endpoint (LU) of the X-ray sensor, a left lower endpoint (LL) of the X-ray sensor, a right upper endpoint (RU) of the X-ray sensor, and a right lower endpoint (RL) of the X-ray sensor, and a vertical centerline of the X-ray sensor are stored. The analyzing unit is configured for calculating a vertical left line between the left upper endpoint (LU) and the left lower endpoint (LL), wherein the vertical left line is bent due to a presence of the patient. The analyzing unit is further configured for calculating a vertical right line between the right upper endpoint (RU) and the right lower endpoint (RL), wherein the vertical right line is bent due to the presence of the patient. Furthermore, the analyzing unit is configured for calculating a first intersection point (P1) between the detected course of the line and the calculated vertical left line, and wherein the analyzing unit is configured for calculating a second intersection point (P2) between the detected course of the line and the calculated vertical right line. Moreover, the analyzing unit is configured for calculating a left angle between a line segment from the left upper endpoint (LU) to the calculated first intersection point (P1) and a line segment from the calculated first intersection point (P1) to the left lower endpoint (LL). The analyzing unit is configured for calculating a right angle between a line segment from right upper endpoint (RU) to the calculated second intersection point (P2) and a line segment from the calculated second intersection point (P2) to the right lower endpoint (RL), wherein the analyzing unit is configured for determining whether the left angle and the right angle are equal.

If the left angle and the right angle are equal, the patient position and/or the patient rotation of the patient corresponds to the predetermined reference parameter. If the left angle and the right angle are not equal, the patient position and/or the patient rotation of the patient needs to be corrected. The left angle may be a left side angle at a left side of the patient and the right angle may be a right side angle at a right side of the patient. The optical arrangement may be configured for creating the feedback signal embodied as a control signal for the X-ray system and/or for the patient positioning system, when the optical arrangement has been determined (calculated) that the left angle and the right angle are not equal. For instance, the angles are equal when the patient is symmetrically aligned with the centerline of the X-ray sensor. The calculating of the vertical left line may be done when no patient is located in front of the X-ray sensor, in this case the vertical lines (left and right) run from the right upper endpoint (RL) to the right lower endpoint (RU) in a straight line. A bending of the vertical lines (left and/or right vertical line) may occur, when a patient is present in front of the X-ray sensor and the intersection points P1 and P2 are calculated, wherein these intersection points P1 and P2 may be used as new locus points for the vertical left line and/or the vertical right line. In particular, the bending of the vertical lines is caused due to the calculation of the intersection points P1 and P2. The intersection points may be detected by the detector of the optical arrangement. For different patients the intersection points P1 and P2 and therefore the bending course of the vertical lines may be different. In particular, the optical arrangement may be configured to calculate the intersection points P1 and P2, when the horizontal laser line is detected and analyzed (by the optical arrangement, preferably by the analyzing unit). The horizontal laser line may analyzed from side to side and the part of the horizontal laser line which is bent due to presence of a patient, the two extremes of the bend lines may be considered as P1 and P2. For instance, this calculation and/or analyzing of P1 and/or P2 may be performed by the analyzing unit, preferably by a computation carried out by a processor. In particular, the bend laser line may be determined and afterwards the analyzing unit calculates the intersection points P1 and P2.

According to an exemplary embodiment of the invention, the method for determining a patient position and/or a patient rotation of a patient to be X-rayed by the X-ray system may further comprise storing in the optical arrangement spatial coordinates of a left upper endpoint (LU) of the X-ray sensor, a left lower endpoint (LL) of the X-ray sensor, a right upper endpoint (RU) of the X-ray sensor, and a right lower endpoint (RL) of the X-ray sensor, and a vertical centerline of the X-ray sensor. Further, the method comprises calculating a vertical left line between the left upper endpoint (LU) and the left lower endpoint (LL) using the analyzing unit, wherein the vertical left line is bent due to a presence of the patient. Calculating a vertical right line between the right upper endpoint (RU) and the right lower endpoint (RL) using the analyzing unit, wherein the vertical right line is bent due to the presence of the patient. Further method steps may comprise calculating by the analyzing unit a first intersection point (P1) between the detected course of the line and the calculated vertical left line, and calculating a second intersection point (P2) between the detected course of the line and the calculated vertical right line. The method may further comprise calculating, using the analyzing unit, a left angle between a line segment from the left upper endpoint (LU) to the calculated first intersection point (P1) and a line segment from the calculated first intersection point (P1) to the left lower endpoint (LL), and calculating a right angle between a line segment from the right upper endpoint (RU) to the calculated second intersection point (P2) and a line segment from the calculated second intersection point (P2) to the right lower endpoint (RL). Further, the method comprises determining whether the left angle and the right angle are equal using the analyzing unit. Depending on the determination of the equality or non-equality of the angles the method may further comprises the step of determining whether the patient position and/or the patient rotation is correct or not. In particular, the patient position may be determined by the shifting of P1 and P2 and the patient rotation is determined by the angles formed at P1 and P2. For instance, if the angles are not equal the patient is rotated. If the intersection points P1 and P2 are not symmetrically spaced apart from the centerline of the X-ray sensor the patient position is not correct. In FIGS. 3 and 4 a detailed determination of the patient position and/or patient rotation is illustrated.

According to an exemplary embodiment of the invention, the feedback signal is embodiment as a control signal, which is configured for controlling the patient position and/or the patient rotation based on a difference between the left angle and the right angle determined by the analyzing unit.

The controlling of the patient position and/or rotation may be initiated when the control signal is received by the X-ray system and/or the patient positioning system. The control signal may be used for indicating whether the patient position and/or the patient rotation is correct with respect to the reference parameter, wherein the reference parameter may be the centerline of the X-ray sensor. For instance, if the difference between the angles is zero, the control signal may indicate that no change of the patient position and/or patient rotation is necessary. Accordingly, the patient positioning system may not change the position and/or rotation of the patient. Contrary, if a difference between the angles is determined the patient position and/or the patient rotation has to be changed and the control signal controls the patient positioning system such that a change of the patient position and/or patient rotation may be initiated, carried out.

According to an exemplary embodiment of the invention, the method for determining a patient position and/or a patient rotation of a patient to be X-rayed by the X-ray system may further comprise a step of controlling, using the analyzing unit, the patient position and/or the patient rotation of the patient based on a difference between the left angle and the right angle, wherein the step may further comprise generating a feedback signal which is embodied as a control signal for performing the above mentioned controlling.

According to an exemplary embodiment of the invention, the analyzing unit is configured for detecting gaps in the course of the laser line, which gaps are created due to a presence of the patient. The analyzing unit is further configured for detecting a left endpoint (L) of the patient using a line detecting algorithm, wherein the left endpoint (L) corresponds to a left point on the course of the laser line at which a horizontal part of the laser line ends. Further, the analyzing unit is configured for detecting a right endpoint (R) of the patient using the line detecting algorithm, wherein the right endpoint (R) corresponds to a right point on the course of the laser line at which a horizontal part of the laser line ends. In the optical arrangement, spatial coordinates of the vertical centerline of the X-ray sensor are stored. Furthermore, the analyzing unit is configured for calculating a middle point between the left endpoint (L) and the right endpoint (R), wherein the analyzing unit is configured for calculating whether the middle point is located on the vertical centerline of the X-ray sensor.

If the middle point is located on the vertical centerline of the X-ray sensor the patent position is correct. If the middle point is not located on the vertical centerline of the X-ray sensor, the patent position needs to be corrected, and the feedback signal is configured for indicating that a correction of the patient position is necessary. In other words, the analyzing unit may be configured for detecting a left endpoint, which corresponds to a left end of the straight horizontal laser line next to the detected (changed) course of the laser line. The analyzing unit may be configured for detecting a right endpoint, which corresponds to a right end of the straight horizontal laser line next to a right side of the beginning/end of the detected (changed) course of the laser line. The left endpoint (L) of the patient may corresponds to a left sided point on the course of the laser line where a horizontal part of the course of the laser line ends and a gap begins. Contrary, the right endpoint (R) of the patient corresponds to a right sided point on the course of the laser line where a horizontal part of the course of the laser line begins and a gap ends (viewed from the left to the right). The spatial coordinates of the vertical centerline of the X-ray sensor may be stored in the analyzing unit. Alternatively, the spatial coordinates may be received by the optical arrangement from an external data storage. In the FIGS. 6 and 7, a detailed correction of the patient position may be described.

According to an exemplary embodiment of the invention, the method for determining a patient position and/or a patient rotation of a patient to be X-rayed by the X-ray system may further comprise the steps of detecting gaps in the course of the laser line by the analyzing unit, which gaps are created due to a presence of the patient. The method may further comprise detecting a left endpoint (L) of the patient using a line detecting algorithm, wherein the left endpoint (L) corresponds to a left point on the course of the laser line at which a horizontal part of the laser line ends and detecting a right endpoint (R) of the patient using the line detecting algorithm, wherein the right endpoint (R) corresponds to a right point on the course of the laser line at which a horizontal part of the laser line ends. Further, the method may comprise storing in the optical arrangement spatial coordinates of the vertical centerline of the X-ray sensor, and calculating a middle point between the left endpoint (L) and the right endpoint (R) and calculating whether the middle point is located on the vertical centerline of the X-ray sensor. The above-mentioned detecting and calculating steps may be performed by the analyzing unit.

According to an exemplary embodiment of the invention, the generated feedback signal is embodied as a control signal, which is configured for controlling the determined patient position based on a difference between the middle point to the vertical centerline of the X-ray sensor calculated by the analyzing unit.

The controlling of the patient position and/or rotation may be initiated when the control signal is received by the X-ray system and/or the patient positioning system. For instance, if the there exists a difference between the middle point and the centerline of the X-ray sensor, the patient position may need to be corrected. For instance, a sign of the difference may indicate whether the patient has to move left or right, wherein a positive sign the patient may need to move left and a negative sign means that the patient may need to move right. The magnitude of the difference may indicate how far the patient needs to move or be moved. Hence, the generated feedback signal may be configured to for controlling based on the sign of the difference and the magnitude of the difference and/or the generated feedback signal may at least be configured to indicate the sign of the difference and/or the magnitude of the difference. Contrary, if there does not exist a difference there is no correction of the patient position necessary. Hence, the feedback signal (embodied as the control signal) may firstly indicate whether a correction is necessary, wherein this may be indicated to the patient and/or staff member by an optical, haptic, acoustic feedback signal. Secondly, the feedback signal may be used for controlling the patient position (if detected incorrect), wherein the position is controlled by the X-ray system itself and/or by the patient positioning system, or where the patient is asked to move left or right by automated voice commands, until the position is correct.

According to an exemplary embodiment of the invention, the method for determining a patient position and/or a patient rotation of a patient to be X-rayed by the X-ray system may further comprise generating a feedback signal embodied as a control signal and controlling the determined patient position based on a difference between the middle point to the vertical centerline of the X-ray sensor calculated by the analyzing unit. In particular, the method comprises controlling the determined patient position based on the sign of the difference and/or on the magnitude of the difference.

According to an exemplary embodiment of the invention, the analyzing unit may be configured for detecting gaps in the course of the laser line using a line-detecting algorithm, which gaps are formed due to the shape of the patient. Further, the analyzing unit may be configured, using a line-detecting algorithm, for determining a length of the gap of the course of the laser line at a left end position of the patient and at a right end position of the patient. Furthermore, the analyzing unit may be configured for calculating from the determined length of the left end position of the patient and from the determined length of the right end position of the patient the patient rotation.

If the length of the gap at the left end position is not equal to the length of the gap at the right end position, the patient rotation may need to be corrected. Accordingly, if the length of both gaps are equal the patient rotation is correct, wherein a correct patient rotation may be defined such that the left-right axis of the patient is parallel to the plane of the X-ray sensor. The left right axis of the patient shall be understood to describe an axis extending from the left side of the patient through the right side of the patient, wherein this axis extends horizontally, which means perpendicular to the centerline of the patient. A detailed illustration of the determination of the patient rotation is described by FIG. 7.

According to an exemplary embodiment of the invention, the method for determining a patient position and/or a patient rotation of a patient to be X-rayed by the X-ray system may further comprise the steps of detecting gaps in the course of the laser line using a line detecting algorithm, which gaps are formed due to the shape of the patient. Using a line detecting algorithm, for determining a length of the gap of the course of the laser line at a left end position of the patient and at a right end position of the patient, and calculating from the determined length of the left end position of the patient and from the determined length of the right end position of the patient the patient rotation. These steps may be performed by the analyzing unit.

According to an exemplary embodiment of the invention, the feedback signal is embodied as a control signal, which is configured for controlling the determined patient rotation based on a gap difference between the length of the left end position of the patient and the length of the right end position of the patient.

For instance, if there exists a gap difference, the feedback signal (control signal) may control the X-ray system and/or patient positioning system for correcting the patient rotation. In the figures, a detailed correction of the patient rotation is described.

According to an exemplary embodiment of the invention, the method for determining a patient position and/or a patient rotation of a patient to be X-rayed by the X-ray system may further comprise the step of generating the feedback signal which is embodied as a control signal and controlling, using the generated feedback signal, the determined patient rotation based on a gap difference between the length of the left end position of the patient and the length of the right end position of the patient.

According to an exemplary embodiment of the invention, the analyzing unit is configured for detecting an inhalation status of the patient. The analyzing unit is configured for determining the inhalation status after the determination of the patient position and after the determination that the patient position corresponds to the predetermined reference parameter.

Before the analyzing unit may determine the inhalation status, the patient position and/or the patient rotation may be determined to be correct. Depending on the inhalation status, the quality of the X-ray image may be influenced. For instance, when the muscular structure of the chest and/or the back of a patient should be clearly visible in the X-ray image, or for example a fully expanded lung, a complete inhalation is preferred. The inhalation status may be determined after the patient position and/or patient rotation have been determined to be correct, such that the determination of the inhalation status may not be effected by failure due to patient position and/or rotation. A pseudo lung volumetric temporal profiling may be obtained for detecting the optimum inhalation point, wherein the decision point for image acquisition may be based on the lung volume, hence on the inhalation. For instance, the optimum inhalation point may be the maximum inhalation. In the figures, a detailed correction of the patient inhalation status is described. For instance, FIG. 5 illustrates a determination of the inhalation status of the patient.

According to an exemplary embodiment of the invention, the method for determining a patient position and/or a patient rotation of a patient to be X-rayed by the X-ray system may further comprise the step of detecting an inhalation status of the patient.

Determining the inhalation status may be performed after the determination of the patient position and after the determination that the patient position corresponds to the predetermined reference parameter. The determining steps may be performed by the analyzing unit.

According to an exemplary embodiment of the invention, the analyzing unit may be configured for determining the inhalation status based on a breathing cycle derived from a change of an approximation of an axial cross section area under the detected course of the laser line, at consecutive time points. The analyzing unit may be configured for determining the axial cross section area for an exhalation and an inhalation of the patient.

The breathing cycle may be determined for a period of time, such that a decision for an optimum X-ray imaging point may be derived from the inhalation status. The breathing cycle may comprise an inhalation course and an exhalation course of the patient over the period of time. When the breathing cycle is determined, a pseudo volumetric temporal profile of the lung of the patient may be derived, based on the inhalation and the exhalation of the patient.

According to an exemplary embodiment of the invention, the method for determining a patient position and/or a patient rotation of a patient to be X-rayed by the X-ray system may further comprise the step of determining the inhalation status based on a breathing cycle derived from a change of an approximation of an axial cross section area under the detected course of the laser line, at consecutive time points. The method may further comprise the step of determining the axial cross section area for an exhalation and an inhalation of the patient. The method steps may be performed by the analyzing unit.

According to a second aspect of the invention, a system for controlling a patient position and/or a patient rotation of a patient to be X-rayed by an X-ray device is described. The system comprises the X-ray device for generating an X-ray image of the patient. The X-ray device comprises an X-ray source, an X-ray sensor. Further, the system comprises an optical arrangement, according to any of embodiments as described above, wherein the system is configured for controlling the patient position and/or the patient rotation of the patient based on the feedback signal generated by the optical arrangement.

The X-ray sensor may be arranged opposite to the X-ray source, such that between the X-ray source and the X-ray sensor the patient may be arranged for being X-rayed. The distance between the X-ray sensor and the X-ray source may depend on the respective embodiment of the X-ray device available. In particular, the X-ray source is arranged in such a manner that X-ray radiation emitted by the X-ray source is emitted on the patient and the X-ray sensor can detect residual X-ray radiation, which has been changed due to the anatomy of the patient.

According to an exemplary embodiment of the invention, a method for controlling a patient position and/or a patient rotation of a patient to be X-rayed by an X-ray device may comprise the steps of generating an X-ray image of the patient by the X-ray device, wherein the generating of the X-ray image may be performed by the X-ray device using an X-ray source and an X-ray sensor. The method may further comprise the step of controlling the patient position and/or the patient rotation of the patient based on the feedback signal generated by the optical arrangement, which has been described with the embodiments hereinabove.

According to an exemplary embodiment of the invention, the optical arrangement is arranged at the side of the X-ray source. In this arrangement, the patient to be X-rayed by the X-device is placed between the X-ray sensor on one side and on the other side the X-ray source together with the optical arrangement.

According to an exemplary embodiment of the invention, the patient position and/or the patient rotation is determined prior to a triggering of the X-ray image. For avoiding failures in the X-ray images, hence for providing an X-ray image having a high quality, the patient position and/or the patient rotation and/or the patient inhalation may be determined before the X-ray image may be triggered. The method for controlling a patient position and/or a patient rotation of a patient to be X-rayed by the X-ray device may further comprise determining the patient position and/or the patient rotation prior to a triggering of the X-ray image.

According to an exemplary embodiment of the invention, the optical arrangement is configured for determining an inhalation status of the patient, and wherein the system is configured to trigger a start of an X-ray imaging process based on a result of the inhalation status detection carried out by the optical arrangement. In particular, the X-ray device may be configured to trigger a start of an X-ray imaging process based on a result of the inhalation status detection. As described with the embodiments hereinabove, the inhalation status may be determined based on a breathing cycle derived from a change of an approximation of an axial cross section area under the detected course of the laser line, at consecutive time points. This breathing cycle may be used to trigger the start of the X-ray imaging process.

The method for controlling a patient position and/or a patient rotation of a patient to be X-rayed by the X-ray device may further comprise triggering a start of an X-ray imaging process based on a result of the inhalation status detection carried out by the optical arrangement. In particular, the triggering of a start of an X-ray imaging process based on a result of the inhalation status detection.

According to third aspect of the invention, a method for determining a patient position and/or a patient rotation, of a patient to be X-rayed with an X-ray device, comprises the steps of emitting a horizontal laser line by a laser source onto the patient, detecting a course of the laser line at on the patient by a detector, wherein the detector and the laser source are vertically spaced apart from each other. The method further comprises the steps of determining the patient position and/or the patient rotation, based on an analysis of the detected course of the laser line by an analyzing unit, validating whether the determined patient position and/or the patient rotation corresponds to a predetermined reference parameter by the analyzing unit, and providing a feedback signal based on a result of the validation by the analyzing unit. Spatial coordinates of a vertical centerline of an X-ray sensor of the X-ray system are stored. The determined patient position and/or patient rotation is compared with the stored spatial coordinates by the analyzing unit. The vertical centerline of the X-ray sensor is the reference parameter.

The horizontal laser line may be emitted onto a body surface of the patient, in particular onto the chest or the back and the detector detects the course of the laser line on the body surface of the patient.

According to an exemplary embodiment of the invention, the method further comprises the step of controlling the patient position and/or patient rotation, using the feedback signal, which is configured as a control signal, wherein the control signal is received by a patient positioning system for changing the patient position and/or patient rotation upon receipt of the control signal.

The controlling may comprise the generating of the control signal (feedback signal) and may comprise the controlling of the change of the patient position by controlling the patient positioning system. On the contrary, the controlling may only comprise the generating of the control signal and the patient positioning system may use the control signal According to another aspect of the present invention, a program element for determining a patient position and/or a patient rotation, of a patient to be X-rayed with an X-ray device, is presented. The program element, when being executed by a processor of an optical arrangement presented herein, is adapted to cause the optical arrangement to emit a horizontal laser line by the laser source onto the patient, detect a course of the laser line on the patient by the detector, determine the patient position and/or the patient rotation, based on an analysis of the detected course of the laser line by the analyzing unit, validate whether the determined patient position and/or the patient rotation corresponds to a predetermined reference parameter by the analyzing unit, provide a feedback signal based on a result of the validation by the analyzing unit.

The computer program element may be part of a computer program, but it can also be an entire program by itself. For example, the computer program element may be used to update an already existing computer program to get to the present invention.

The program element may be stored on a computer readable medium. The computer readable medium may be seen as a storage medium, such as for example, a USB stick, a CD, a DVD, a data storage device, a hard disk, or any other medium on which a program element as described above can be stored.

BRIEF DESCRIPTION OF THE DRAWINGS

The aspects defined above and further aspects of the present invention are apparent from the examples of embodiment to be described hereinafter and are explained with reference to the examples of embodiment. The invention will be described in more detail hereinafter with reference to examples of embodiment but to which the invention is not limited.

DETAILED DESCRIPTION OF EMBODIMENTS

Figure 1:
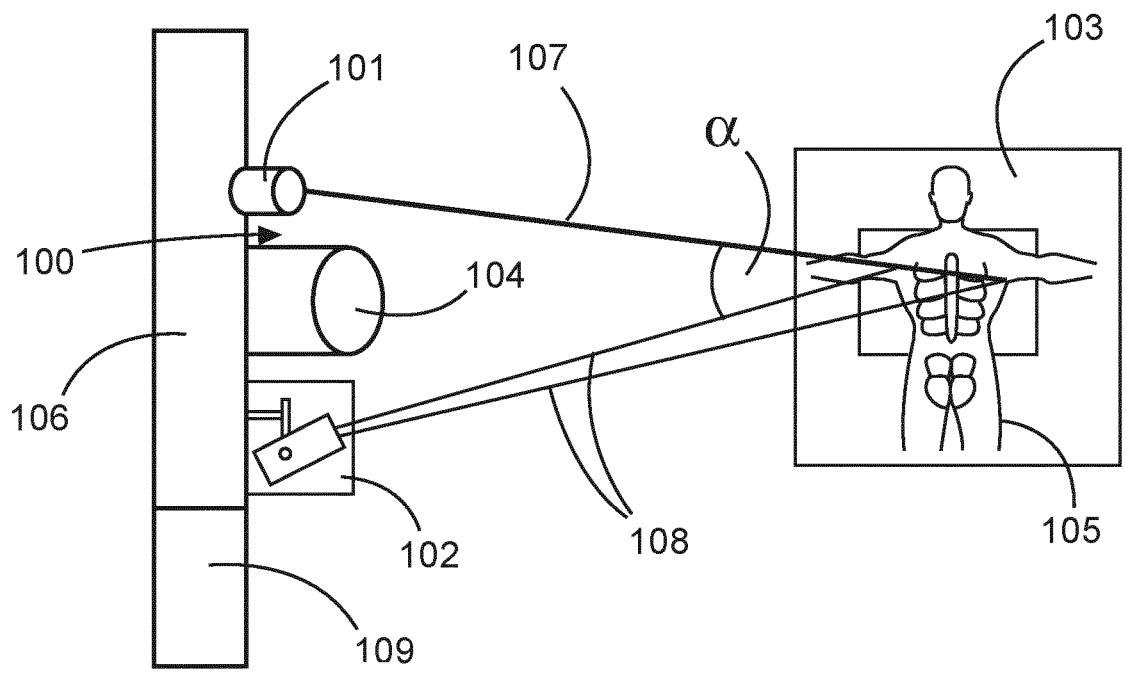
FIG. 1 illustrates an optical arrangement and an X-ray system according to an exemplary embodiment of the invention.

FIG. 1 illustrates an optical arrangement (100) for an X-ray system (106) for determining a patient position and/or a patient rotation of a patient (105) to be X-rayed by the X-ray system (106). As can be seen from FIG. 1, the optical arrangement (100) comprises a laser source (101) and a detector (102) vertically spaced apart from the laser source (101). In other words, the detector is positioned along the vertical direction below the laser source. Thus, the detector is positioned at another, lower vertical height as compared to the laser source. The positions of the laser source and the detector may be interchangeable, such that the detector may be positioned along the vertical direction above the laser source. As can be seen in FIG. 1, the vertical arrangement of the laser source (101) and the detector (102) is a vertical arrangement to the horizon and/or perpendicular to the ground plane, at which the optical arrangement (100), preferably with the X-ray system, is used and applied. In particular, the vertical arrangement is parallel to a centerline of the patient (105), which centerline extends from the head to the feet of the patient (105).

The detector (102) may be a camera, a CCD sensor, or any other suitable optical system able to detect a laser line and/or radiation emitted from a laser line on a patient. The laser source (101) is configured for emitting a horizontal laser line (107) onto the patient (105), wherein the detector (102) is configured for detecting a course of the laser line (107)

emitted onto the patient (105). As is understood by the skilled reader, the horizontal laser line (107) extends, when being emitted, within 3D space parallel to the horizon and/or parallel to the ground plane, at which the optical arrangement (100), preferably with the X-ray system, is used and applied. An analyzing unit (109) is configured for determining the patient position and/or the patient rotation of the patient (105), based on an analysis of the detected course of the laser line (107). Further, the analyzing unit (109) is configured for validating whether the determined patient position and/or patient rotation of the patient (105) corresponds to a predetermined reference parameter, and wherein the analyzing unit (109) is configured for generating a feedback signal based on a result of the validation. The laser source (101) is arranged to emit the laser line (107) along an emitting direction, which emitting direction extends along an imaginary line from the laser source (101) to the patient (105). As can be seen in FIG. 1, the emitting direction of the laser line (107) is illustrated as a visible laser beam (107). The detector (102) is arranged to detect the course of the laser line (107) along a detection direction (108), which detection direction (108) extends along an imaginary line from the detector (102) to the patient (105). In FIG. 1, the detecting direction (108) is illustrated as two lines (108), which illustrate a viewable area of the detector for detecting the laser line (107) on the patient (105). The emitting direction of the laser source (102) and the detection direction (108) of the detector (102) form an angle (α) in a range between 40 to 45 degrees. The analyzing unit (109) may generate the feedback signal, which is embodied as a control signal configured for controlling the patient position and/or patient rotation when being received by an X-ray system or a patient positioning system. As can be seen in FIG. 1, the detector (102) is arranged below the laser source (101), an arrangement in the other way around may also be possible. Further, a system (106) for controlling a patient position and/or a patient rotation of a patient (105) to be X-rayed by an X-ray device is illustrated. The system comprising the X-ray device for generating an X-ray image of the patient, comprising an X-ray source (104) and an X-ray sensor (103). The system (106) further comprises the above described optical arrangement (100) and wherein the system (106) is configured for controlling the patient position and/or the patient rotation of the patient (105) based on the feedback signal generated by the optical arrangement (100). The detector (102) of the optical arrangement (100) may be arranged below the X-ray source (104) and the laser source (101) of the optical arrangement (100) may be arranged above the X-ray source (104), or vice versa. The analyzing unit (109) may also be part of the X-ray system. As can be seen in FIG. 1, the patient (105) is positioned in front of the X-ray sensor (103) of the X-ray system and depending on the position and/or the rotation of the patient (105) in front of the X-ray sensor (103) the generated X-ray image may be influenced. Hence, the patient (105) should be preferably non-rotated and symmetrically aligned in front of the X-ray sensor (105). In FIG. 1, the patient (105) is arranged in the middle of the X-ray sensor (103), wherein a centerline of the patient (105) is parallel to a centerline of the X-ray sensor (103), wherein the centerline of the X-ray sensor (103) extends from the top to the bottom of the X-ray sensor.

Figure 2:
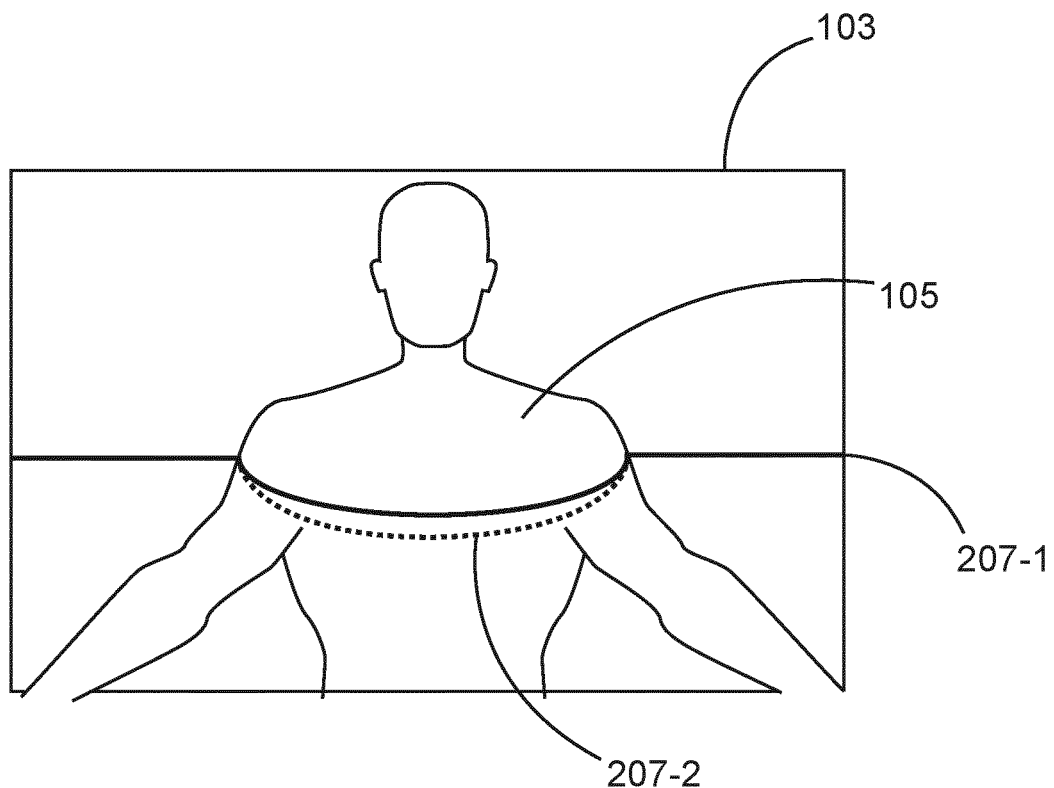
FIG. 2 illustrates a horizontal laser line used in an exemplary embodiment of the invention.

FIG. 2 illustrates a laser line (207) that is horizontally emitted onto a patient (105). The patient (105) is positioned in front of the X-ray sensor (103) and the optical arrangement (100) emits the laser line (207) onto the patient (105). The course of the laser line (207) changes due to the shape of the patient (105). As can be seen in FIG. 2, the course of the continuous laser line (207-1) differs from the course of the broken line (207-2), wherein the difference of the course between these two laser lines (207-1, 207-2) may be based on the patient position and/or the patient rotation and/or on the patient inhalation status. In particular, the difference between the continuous laser line (207-1) and the changed laser line (207-2) is caused by the presence of the patient. Both laser lines (207-1, 207-2) may be emitted laser lines of the laser source which extends horizontally, wherein as can be seen in FIG. 2 the laser lines (207-1, 207-2) are straight laser lines (207-1, 207-2) at the right and left side of the patient. The course of the laser lines (207-1, 207-2) is not bend when there is no patient present, hence the course laser lines (207-1, 207-2) may emitted partially on the X-ray sensor (103) (in the back of the patient). Contrary, if the patient is present the laser lines (207-1, 207-2) are bend, which can be seen in FIG. 2, where the patient is present both laser lines (207-1, 207-2) are bend.

Figure 3:
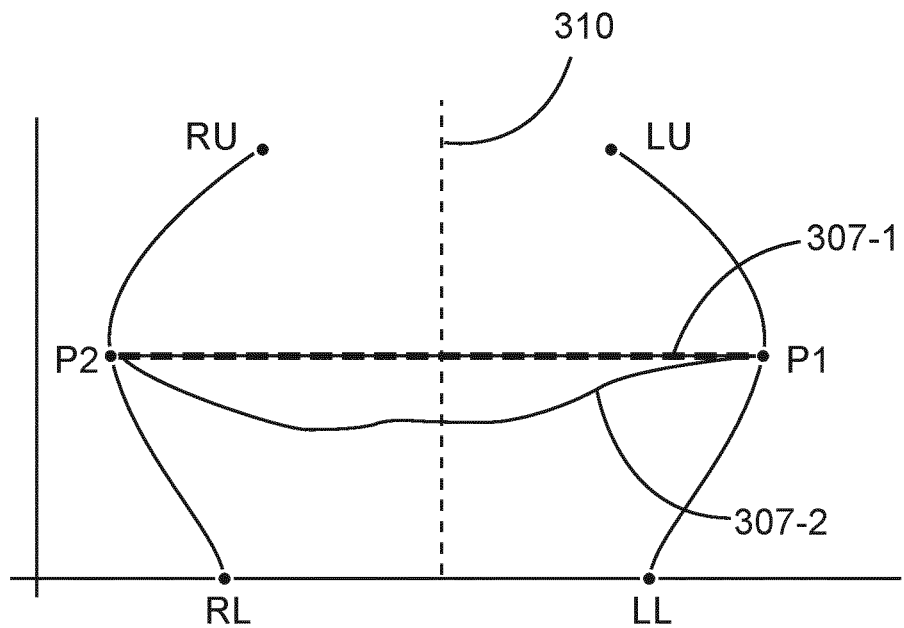
FIG. 3 illustrates the determination of a patient position and/or patient rotation according to an exemplary embodiment of the invention.

FIG. 3 illustrates the determination of a patient position and/or a patient rotation according to an exemplary embodiment of the invention. In particular, FIG. 3 illustrates the in the optical arrangement stored spatial coordinates of a vertical centerline (310) of an X-ray sensor of the X-ray system, wherein the analyzing unit is configured for comparing the determined patient position and/or patient rotation with the stored spatial coordinates, wherein the vertical centerline (310) of the X-ray sensor is the reference parameter.

Further, in the optical arrangement spatial coordinates of a left upper endpoint (LU) of the X-ray sensor, a left lower endpoint (LL) of the X-ray sensor, a right upper endpoint (RU) of the X-ray sensor, and a right lower endpoint (RL) of the X-ray sensor are stored. The analyzing unit is configured for calculating a vertical left line between the left upper endpoint (LU) and the left lower endpoint (LL), wherein the vertical left line is bent due to a presence of the patient. The analyzing unit is configured for calculating a vertical right line between the right upper endpoint (RU) and the right lower endpoint (RL), wherein the vertical right line is bent due to the presence of the patient. Further, the analyzing unit is configured for calculating a first intersection point (P1) between the detected course of the laser line (307-2) and the calculated vertical left line, and calculating a second intersection point (P2) between the detected course of the laser line (307-2) and the calculated vertical right line. If the patient (105) stands in front of the X-ray sensor (103) the laser line (307) will be placed on the patients chest and/or back. The optical arrangement may analyze the course of the laser line (307) on the patient and may determine patient position and/or patient rotation and determine whether this is in accordance with a reference parameter, which may be the centerline (310) of the X-ray sensor (103). The laser line (307-2) represents the laser line when placed on the chest of the patient. Initially the two vertical left and right lines are anchored at the top and the bottom. In FIG. 3, the vertical left line and vertical right line are bend due to a presence of the patient. In this manner the vertical left and vertical right line accommodate the profile of the patient. The intersection points (P1, P2) may be endpoints of the profile of the patient and are considered as the new locus for the vertical left line and the vertical right line, respectively. In particular, the optical arrangement (100) may be configured to calculate the intersection points (P1 and P2), when the course of the laser line (307-2) is detected and analyzed (by the optical arrangement, preferably by the analyzing unit). The course of the laser line (307-2) may analyzed from side to side and the part of the horizontal laser line (307) which is bent due to presence of a patient, the two extremes of the bend laser line (307-2) may be considered as P1 and P2. In particular, the patient position may be determined by the shifting of P1 and P2 and the patient rotation is determined by the angles formed at P1 and P2. If the intersection points P1 and P2 are not symmetrically spaced apart from the centerline of the X-ray sensor the patient position is not correct. The laser line (307-1) illustrates a horizontal laser line (307-1) when no patient is present in front of the X-ray sensor (103).

Figure 4:
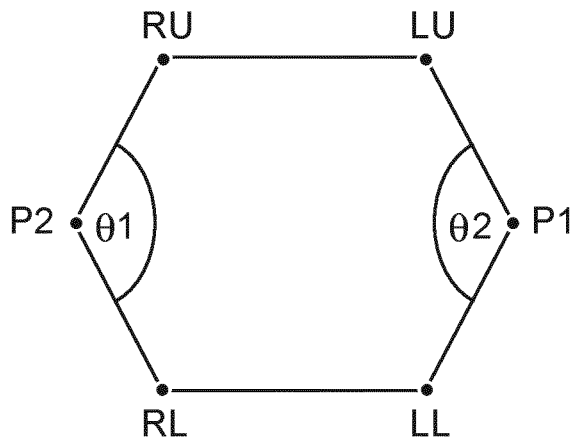
FIG. 4 illustrates the determination of a patient position and/or patient rotation according to an exemplary embodiment of the invention.

FIG. 4 illustrates the determination of a patient position and/or a patient rotation according to an exemplary embodiment of the invention. In particular, FIG. 4 illustrates a calculating of a left angle (Θ2) between a line segment from the left upper endpoint (LU) to the calculated first intersection point (P1) and a line segment from the calculated first intersection point (P1) to the left lower endpoint (LL). Further, a calculating of a right angle (Θ1) between a line segment from the right upper endpoint (RU) to the calculated second intersection point (P2) and a line segment from the calculated second intersection point (P2) to the right lower endpoint (RL) is illustrated. The analyzing unit (109) is configured for determining whether the left angle (Θ2) and the right angle (Θ1) are equal. The left angle (Θ2) and the right angle (Θ1) are subsequently determined between the line segments. If the patient position is symmetrically aligned with the centerline (310) of the X-ray sensor (103) then the angles formed by the curves should be equal. If this condition does not satisfy than the feedback signal will be given to the patient (105), patient positioning system, and/or to a user (medial staff) for correcting the patient position. Geometrically the determination and calculation of the line segments and the left angle (Θ2) and the right angle (Θ1) can be represented by the sides and angles of a hexagon. In case of a rotation of the patient (105), either the left angle (Θ2) is larger than the right angle (Θ1) or the left angle (Θ2) is smaller the right angle (Θ1) and from this inequality of angles the rotation error may be determined. For instance, if the angles (Θ1), (Θ2) are not equal the patient is rotated.

Figure 5:
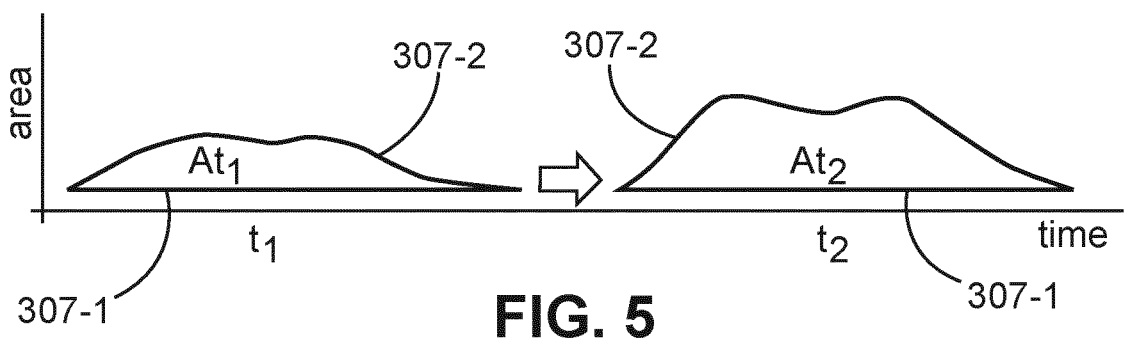
FIG. 5 illustrates the determination of an inhalation status according to an exemplary embodiment of the invention.

FIG. 5 illustrates a detection of an inhalation status of the patient (105), and wherein the analyzing unit (109) is configured for determining the inhalation status after the determination of the patient position and after the determination that the patient position corresponds to the predetermined reference parameter. The analyzing unit (109) is configured for determining the inhalation status based on a breathing cycle derived from a change of an approximation of an axial cross section area (At1, At2) under the detected course of the laser line (307) at consecutive time points (t1, t2). Further, the analyzing unit is configured for determining the axial cross section area (At1, At2) for an exhalation and an inhalation of the patient. The axial cross section area (At1, At2) is determined between the not changed course of the laser line (307-1) and the course of the changed laser line (307-2), which changes due to a presence of the patient (105). The determined axial cross section area (At1) may correspond to an exhalation of the patient at a time point t1, and the determined axial cross section area (At2) may correspond to an inhalation of the patient at a time point t2. As can be seen in FIG. 5, the approximation of the axial cross section area of the inhalation (At2) may be larger than the approximation of the axial cross section area of the exhalation (At1). The breathing cycle of the patient may be derived using the change in approximation of the axial cross section areas (At1, At2) at consecutive temporal sampling and the displacement of a center of gravity of the respective axial cross section area. The determination of the axial cross section area may be calculated using the following equation $$At_x = h/3[f(x_0) + 2\Sigma_{j=1}^{n/2-1} f(x_{2j}) + 4\Sigma_{j=1}^{n/2} f(x_{2j-}) + f(x_n)].$$

In this equation the variables may be as follows, x0 may be a first value, n may be a number of terms, j may be an incremental variable, x may be data points and h may be a maximum of x. The derived breathing cycle and the determined axial cross section area may be displayed on a screen and/or display, which may be part of the optical arrangement. A digital twin of the patients lung simulating the inhalation and the exhalation may also be presented on the screen for a better visual experience.

Figure 6:
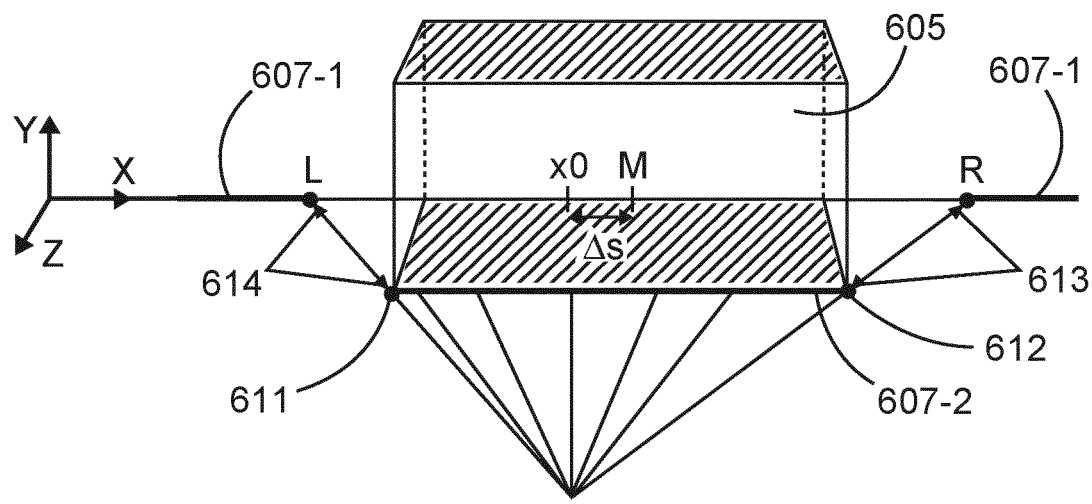
FIG. 6 illustrates the determination of a patient position and/or patient rotation according to an exemplary embodiment of the invention.

FIG. 6 illustrates a detection of gaps (613, 614) in the course of the laser line (607), which gaps (613, 614) are created due to a presence of the patient. The analyzing unit (109) is configured for detecting a left end point (L) of the patient using a line detecting algorithm, wherein the left end point (L) corresponds to a left point on the course of the laser line (607) at which a horizontal part of the laser line (607-1) ends. Further, the analyzing unit (109) is configured for detecting a right end point (R) of the patient using the line detecting algorithm, wherein the right end point (R) corresponds to a right point on the course of the laser line (607) at which a horizontal part of the laser line (607-1) ends. In the optical arrangement spatial coordinates of the vertical centerline (310) of the X-ray sensor (103) are stored. In FIG. 6 the centerline (310) of the X-ray sensor is illustrated by the (x0) coordinate. The analyzing unit (109) is configured for calculating a middle point (M) between the left endpoint (L) and the right endpoint (R), wherein the analyzing unit (109) is configured for calculating whether the middle point (M) is located on the vertical centerline (310) of the X-ray sensor. The gaps (613, 614) may be introduced by the patient in the laser line (607) at the left and right edge of the patient. In FIG. 6, the patient is simplified as a rectangular box. The line detecting algorithm may be used to follow the laser line and to detect gaps (613, 614) in the laser line (607). This algorithm may be performed in real time. The algorithm is used to determine the left and right end of the patient by finding the points (L) and (R) at which the horizontal laser line (607-1) ends. The points (L) and (R) are found as the ends of the horizontal laser line (607-1) just before the gaps (613, 614). The middle point (M) may be calculated and if the middle point (M) does not lie at x=x0 the patient stands off-center, e.g. left or right from the vertical centerline (310) of the X-ray sensor (103), and a correction of the patient position may be necessary. The patient position may be corrected by the x-offset (As) of the middle point (M) in order to be centered. Between the gaps (613, 614) the changed course of the laser line (607-2), changed due to the presence of the patient, may be formed.

Figure 7:
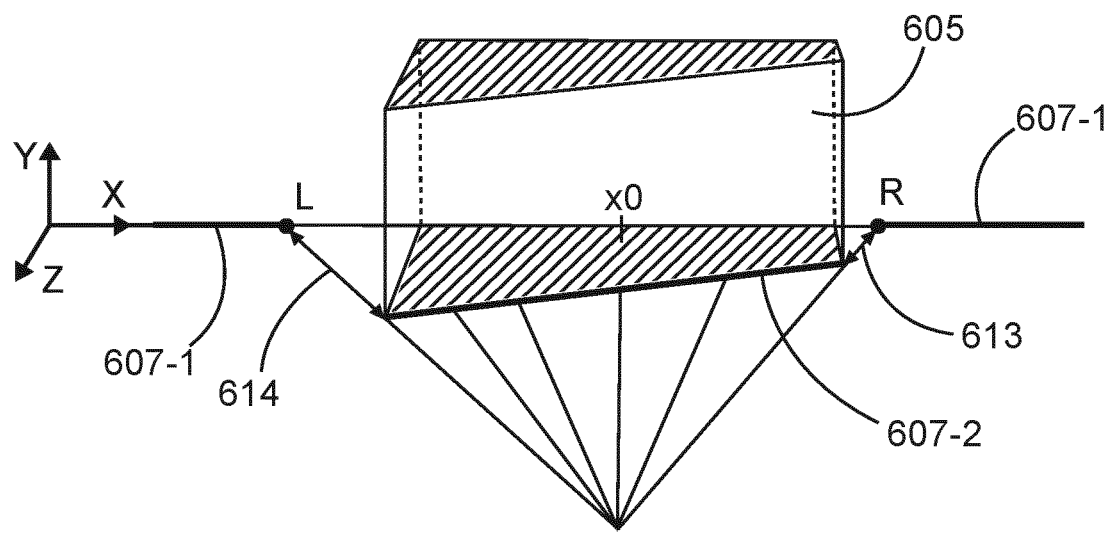
FIG. 7 illustrates the determination of a patient position and/or patient rotation according to an exemplary embodiment of the invention.

FIG. 7 illustrates a detection of gaps (613, 614) in the course of the laser line (607) using a line detecting algorithm, which gaps (613, 614) are formed due to the shape of the patient. The analyzing unit (109) is configured, using a line detecting algorithm, for determining a length of the gap (614) of the course of the laser line (607) at a left end position of the patient and at a right end position of the patient, and wherein the analyzing unit (109) is configured for calculating from the determined length of the left end position of the patient and from the determined length of the right end position of the patient the patient rotation. For instance, if the patient position may be correct, the patient rotation may still need to be corrected. A patient, which is still rotated may introduce gaps of different length at the left and right end of the patient. The left and right end of the patient may be determined using the features as described with FIG. 6 and then to determine the length of the gaps (613, 614) using a line detecting algorithm. The length of the gaps (613, 614) may be detected in real time image processing and the feedback signal may be provided to the patient and/or the patient position system, and/or the user for performing the correction of the patient rotation. For instance, it is determined whether gap (614) is larger than gap (613), which may be expressed by the following equation $$gap(614)-gap(613)>m,$$

further, it may be determined whether gap (614) is smaller than gap (613), which may be expressed by the following equation $$gap(614)-gap(613)<-m,$$

wherein m may be a predetermined fixed error margin m, e.g. m=1 cm. If gap (614) is larger than gap (613) the feedback signal may indicate to the patient (and/or user) to turn right (for narrowing the left gap) as long as the gap (614) is larger than gap (613), wherein in this configuration the patient stands with the back to the X-ray sensor and the right side of the patient may be arranged next to the determined left end point (L). If the gap (614) is smaller than gap (613) than the feedback signal may indicate to the patient to turn left (for narrowing the right gap) as long as the gap (614) is smaller than gap (613). Otherwise, the patient should stand still, wherein the feedback signal may provide no correction signal to the patient, patient positioning system, and/or the user.

Figure 8:
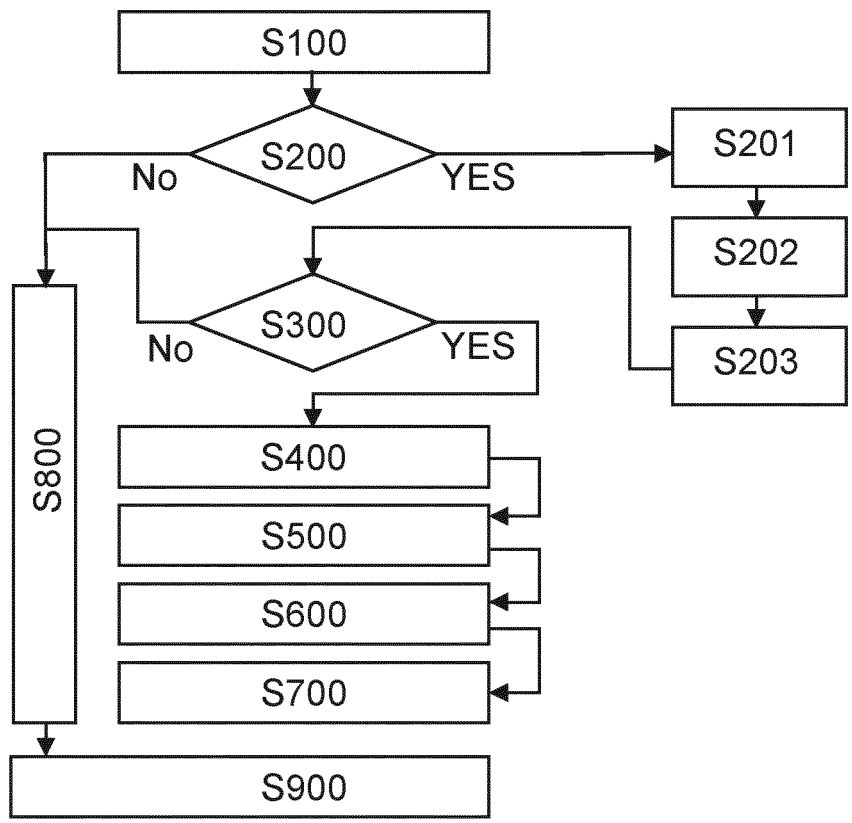
FIG. 8 illustrates a flow diagram of a method for determining a patient position and/or patient rotation according to an exemplary embodiment of the invention.

FIG. 8 illustrates diagram for a determining of a patient position and/or patient rotation according to an exemplary embodiment of the invention, wherein the determining may be integrated into an autonomous workflow integration. In an autonomous imaging scenario, the patient may need to train about the autonomous procedure, which involves initial positioning of the patient, error detection (patient position, patient rotation, and patient inhalation status) and correction through the feedback signal by the analyzing unit (109). FIG. 8 illustrates how the training of the patient, automatic error detection (patient position, patient rotation, and patient inhalation status) and triggering of an X-ray image may be incorporated into an X-ray acquisition workflow. In step (S100) the patient enters the X-ray imaging laboratory. In step (S200) the patient is evaluated for autonomous imaging based on the physical condition. For instance, for evaluating whether a patient is fit enough for autonomous imaging a set of patient evaluation criteria may be need to followed. A first a patient evaluation criteria may be a response time, wherein it is checked if the patient can respond to an instruction successfully with a stipulated and reasonable time, e.g. 5 seconds. A second patient evaluation criteria may be a retry attempts, which means that it is attempt to instruct the patient in case of failed outcomes during training, e.g. maximum of 3 or 5 attempts. A third patient evaluation criteria may be patient disabilities, wherein these disabilities may be categorized as cognitive disability, physical disability due to health condition or age, or other disabilities. In step (S200) the third patient evaluation criteria may be evaluated. If the patient evaluation criteria is fulfilled the method may proceed to step (S201), if not the method proceeds to step (S800). If the patient fulfills the third evaluation criteria in step (S201) the patient may be trained for autonomous imaging. In step (S202) the patient may be informed about initial positioning with respect to the laser line emitted onto the patient, wherein this information may be provided by an interactive video and/or by medical staff. In step (S203) the patient may be trained about the provided feedback signal, which may be haptic, optic, and/or audio feedback, wherein the patient may be trained about the feedback based error correction, with respect to the patient position, patient rotation, and/or patient inhalation status, through a mock dry run and/or video session. When the patient has successfully executed all steps (S201 to S203) than it is proceeded to step (S300). In step (S300) patient response is evaluated and it is determined the suitability for autonomous imaging using the first and second patient evaluation criteria. If these criteria are fulfilled it is proceed with step (S400). In step (S400) the optical arrangement determines the patient position and/or the patient rotation as described with the embodiments mentioned hereinabove. In particular, in step (S400) the method for determining the patient position and/or the patient rotation as described in the various embodiments hereinabove is carried out. After step (S400) it is proceed to step (S500), wherein in this step (S500) a correction of the determined patient position and/or patient rotation may be carried out. In particular, in step (S500) the system for controlling a patient position and/or a patient rotation of a patient to be X-rayed by an X-ray device may be used for controlling and/or correcting the determined patient position and/or patient rotation if it needs to be corrected. When this step has been proceed successfully, step (S600) may be carried out, wherein a triggering of the X-ray imaging may start. In step (S700) the procedure of the X-ray imaging may be completed and an X-ray image may be generated and in step (S900) the image acquisition is completed. If the patient does not fulfil the patient evaluation criteria in step (S200) and/or in step (S300) there may be a manual intervention necessary, wherein the method would proceed to step (S800) and may finish the image acquisition without the steps (S400 to S700). The hereinabove described steps may be performed using a patient training apparatus, wherein this apparatus may be an external part of the X-ray system and/or the X-ray device and/or the optical arrangement. On the other hand, the patient training apparatus may be a training procedure, which may be included in the X-ray system and/or the X-ray device and/or the optical arrangement by software or a data processing unit.

Figure 9:
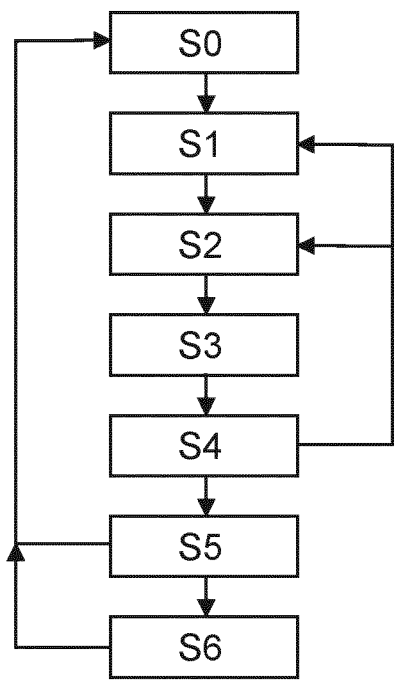
FIG. 9 illustrates a flow diagram of a method for a determining a patient position and/or patient rotation according to an exemplary embodiment of the invention.

FIG. 9 illustrates the method steps for determining a patient position and/or a patient rotation, of a patient to be X-rayed with an X-ray device. The method comprising the steps of (S0) arranging the patient in front of an X-ray sensor of the X-ray device, (S1) emitting a horizontal laser line by a laser source onto the patient, (S2) detecting a course of the laser line on the patient by a detector. The detector and the laser source are vertically spaced apart from each other. Step (S3) comprises determining the patient position and/or the patient rotation, based on an analysis of the detected course of the laser line by an analyzing unit. Step (S4) comprises validating whether the determined patient position and/or the patient rotation corresponds to a predetermined reference parameter by the analyzing unit. In step (S5) a feedback signal is provided based on a result of the validation by the analyzing unit. If the feedback signal indicates that the determined patient position and/or patient rotation does not comply with the reference parameter it may be returned to step (S0) and a rearrangement of the patient in front of the X-ray sensor may be necessary. In step (S4) it may be returned to step (S1) and/or step (S2), for reemitting the laser line onto the patient and/or for redetecting the course of the laser line on the patient. This method steps may be carried out in the method step (S400) of FIG. 8. The method may comprise a further step (S6) for controlling the patient position and/or patient rotation, using the feedback signal which is configured as a control signal, wherein the control signal is received by a patient positioning system for changing the patient position and/or patient rotation upon receipt of the control signal. When step (S6) may be used for controlling the patient position and/or the patient rotation it may be restart with step (S0) for rearranging the patient when the determination of the patient position and/or rotation was not correct. The methods as described with FIGS. 8 and 9 may also comprise the determination of the patient inhalation status.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

LIST OF REFERENCE SIGNS 100 optical arrangement
101 laser source
102 detector
103 X-ray sensor
104 X-ray source
105, 605 patient
106 X-ray system
107 laser line
108 detecting direction
109 analyzing unit
α angle
207-1 laser line
207-2 laser line
310 centerline of X-ray sensor
307-1 horizontal laser line
307-2 laser line
607-1 horizontal laser line
607-2 laser line
611 patient left point
612 patient right point
613, 614 gap
P1, P2 intersection point
RU right upper endpoint
RL right lower endpoint RL
LU left upper endpoint
LL left lower endpoint
L left endpoint
R right endpoint
Θ1, Θ2 angle
x0 centerline of X-ray sensor
M middle point
Δs offset

The invention claimed is:

1. An optical arrangement for an X-ray system for determining a patient position and/or a patient rotation of a patient to be X-rayed by the X-ray system, the optical arrangement comprising:
a laser source configured to emit a laser line onto the patient;
a detector vertically spaced apart from the laser source and configured to detect a course of the laser line emitted onto the patient; and
an analyzer configured to determine the patient position and/or the patient rotation, based on an analysis of the detected course of the laser line,
wherein the analyzer is configured to validate whether the determined patient position and/or patient rotation of the patient corresponds to a predetermined reference parameter, and is configured to generate a feedback signal based on a result of the validation,
wherein spatial coordinates of a vertical centerline of an X-ray sensor of the X-ray system are stored,
wherein the analyzer is configured to compare the determined patient position and/or patient rotation with the stored spatial coordinates, and
wherein the vertical centerline of the X-ray sensor is the reference parameter.

2. The optical arrangement according to claim 1,
wherein the laser source is arranged to emit the laser line along an emitting direction that extends along an imaginary line from the laser source to the patient,
wherein the detector is arranged to detect the course of the laser line along a detection direction that extends along an imaginary line from the detector to the patient,
wherein the emitting direction of the laser source and the detection direction of the detector form an angle in a range between 40 and 45 degrees.

3. The optical arrangement according to claim 1, wherein the generated feedback signal is a control signal configured to control the patient position and/or patient rotation when being received by the X-ray system or a patient positioning system.

4. The optical arrangement according to claim 1,
wherein the spatial coordinates of a left upper endpoint of the X-ray sensor, a left lower endpoint of the X-ray sensor, a right upper endpoint of the X-ray sensor, and a right lower endpoint of the X-ray sensor, and a vertical centerline of the X-ray sensor are stored,
wherein the analyzer is configured to calculate a vertical left line between the left upper endpoint and the left lower endpoint, wherein the vertical left line is bent due to a presence of the patient,
wherein the analyzer is configured to calculate a vertical right line between the right upper endpoint and the right lower endpoint, wherein the vertical right line is bent due to the presence of the patient,
wherein the analyzer is configured to calculate a first intersection point between the detected course of the line and the calculated vertical left line,
wherein the analyzer is configured to calculate a second intersection point between the detected course of the line and the calculated vertical right line,
wherein the analyzer is configured to calculate a left angle between a line segment from the left upper endpoint to the calculated first intersection point and a line segment from the calculated first intersection point to the left lower endpoint,
wherein the analyzer is configured to calculate a right angle between a line segment from the right upper endpoint to the calculated second intersection point and a line segment from the calculated second intersection point to the right lower endpoint,
wherein the analyzer is configured to determine whether the left angle and the right angle are equal.

5. The optical arrangement according to claim 4, wherein the generated feedback signal is a control signal configured to control the patient position and/or the patient rotation based on a difference between the left angle and the right angle determined by the analyzer.

6. The optical arrangement according to claim 1,
wherein the analyzer is configured to detect gaps in the course of the laser line created due to a presence of the patient,
wherein the analyzer is configured to detect a left endpoint of the patient using a line detecting algorithm, wherein the left endpoint corresponds to a left point on the course of the laser line at which a horizontal part of the laser line ends,
wherein the analyzer is configured to detect a right endpoint of the patient using the line detecting algorithm, wherein the right endpoint corresponds to a right point on the course of the laser line at which a horizontal part of the laser line ends,
wherein spatial coordinates of the vertical centerline of the X-ray sensor are stored,
wherein the analyzer is configured to calculate a middle point between the left endpoint and the right endpoint,
wherein the analyzer is configured to calculate whether the middle point is located on the vertical centerline of the X-ray sensor.

7. The optical arrangement according to claim 6, wherein the generated feedback signal is a control signal, which is configured to control the determined patient position based on a difference between the middle point to the vertical centerline of the X-ray sensor calculated by the analyzer.

8. The optical arrangement according to claim 1,
wherein the analyzer is configured to detect gaps in the course of the laser line using a line detecting algorithm, the gaps being formed due to the shape of the patient,
wherein the analyzer unit is configured, using a line detecting algorithm, to determine a length of the gap of the course of the laser line at a left end position of the patient and at a right end position of the patient, and
wherein the analyzer is configured to calculate the patient rotation from the determined length of the left end position of the patient and from the determined length of the right end position of the patient.

9. The optical arrangement according to claim 8, wherein the feedback signal is a control signal, which is configured to control the determined patient rotation based on a gap difference between the length of the left end position of the patient and the length of the right end position of the patient.

10. The optical arrangement according to claim 1,
wherein the analyzer is configured to detect an inhalation status of the patient, and
wherein the analyzer is configured to determine the inhalation status after the determination of the patient position and after the determination that the patient position corresponds to the predetermined reference parameter.

11. A system for controlling a patient position and/or a patient rotation of a patient to be X-rayed by an X-ray device, the system comprising:
the X-ray device for generating an X-ray image of the patient comprising an X-ray source and an X-ray sensor, and
an optical arrangement according to claim 1, and
wherein the system is configured to control the patient position and/or the patient rotation based on the feedback signal generated by the optical arrangement.

12. The system according to claim 11, wherein the optical arrangement is configured to determine an inhalation status of the patient, and wherein the system is configured to trigger a start of an X-ray imaging process based on a result of the inhalation status detection carried out by the optical arrangement.

13. A method for determining a patient position and/or a patient rotation; of a patient to be X-rayed with an X-ray device, the method comprising:
emitting a horizontal laser line by a laser source onto the patient;
detecting a course of the laser line on the patient by a detector, wherein the detector and the laser source are vertically spaced apart from each other;
determining the patient position and/or the patient rotation, based on an analysis of the detected course of the laser line;
validating whether the determined patient position and/or the patient rotation corresponds to a predetermined reference parameter;
providing a feedback signal based on a result of the validation;
wherein spatial coordinates of a vertical centerline of an X-ray sensor of the X-ray system are stored,
wherein the determined patient position and/or patient rotation is compared with the stored spatial coordinates, and
wherein the vertical centerline of the X-ray sensor is the reference parameter.

14. The method according to claim 13, further comprising:
controlling the patient position and/or patient rotation, using the feedback signal which is configured as a control signal, wherein the control signal is received by a patient positioning system for changing the patient position and/or patient rotation upon receipt of the control signal.

* * * * *